United States Patent
Huang et al.

(10) Patent No.: US 10,631,804 B2
(45) Date of Patent: Apr. 28, 2020

(54) HEAT TRANSFER DEVICE, X-RAY DETECTING APPARATUS AND X-RAY IMAGING EQUIPMENT

(71) Applicant: General Electric Company, Schenectady, NY (US)

(72) Inventors: Duzi Huang, Beijing (CN); Weimin Qu, Beijing (CN)

(73) Assignee: General Electric Company, Schenectady, NY (US)

( * ) Notice: Subject to any disclaimer, the term of this patent is extended or adjusted under 35 U.S.C. 154(b) by 34 days.

(21) Appl. No.: 15/114,824

(22) PCT Filed: Jan. 16, 2015

(86) PCT No.: PCT/US2015/011795
§ 371 (c)(1),
(2) Date: Jul. 27, 2016

(87) PCT Pub. No.: WO2015/116409
PCT Pub. Date: Aug. 6, 2015

(65) Prior Publication Data
US 2016/0338658 A1 Nov. 24, 2016

(30) Foreign Application Priority Data
Jan. 28, 2014 (CN) .......................... 2014 1 0041478

(51) Int. Cl.
*A61B 6/00* (2006.01)
*A61B 6/03* (2006.01)
(52) U.S. Cl.
CPC ............ *A61B 6/4488* (2013.01); *A61B 6/032* (2013.01)

(58) Field of Classification Search
CPC ............................. A61B 6/4488; A61B 6/032
(Continued)

(56) References Cited

U.S. PATENT DOCUMENTS

| 2,847,936 A * | 8/1958 | Richter ..................... | F04D 7/06 310/104 |
| 3,136,700 A * | 6/1964 | Poppendiek ............ | G21C 1/22 138/39 |

(Continued)

FOREIGN PATENT DOCUMENTS

| JP | S57-50673 A | 3/1982 |
| JP | 2002-341044 A | 11/2002 |
| WO | 2008/153089 A1 | 12/2008 |

OTHER PUBLICATIONS

International Search Report and Written Opinion for corresponding PCT application No. PCT/US2015/011795; dated May 18, 2015; 11 pages.

(Continued)

*Primary Examiner* — David P Porta
*Assistant Examiner* — Blake C Riddick (57) ABSTRACT

The present invention provides a heat transfer device, an X-ray detecting apparatus and an X-ray imaging equipment. The heat transfer device comprises a first heat transfer loop configured to implement heat transfer with an X-ray detector, a heater configured to heat a heat transfer fluid in the first heat transfer loop, a second heat transfer loop disposed to implement heat transfer with the X-ray detector and a radiator configured to cool the heat transfer fluid in the second heat transfer loop. Hence, heat transfer efficiency can be increased.

7 Claims, 6 Drawing Sheets

(58) Field of Classification Search
USPC ........................................ 250/370.09, 370.15
See application file for complete search history.

(56) References Cited

U.S. PATENT DOCUMENTS

| | | | | |
|---|---|---|---|---|
| 3,354,869 A * | 11/1967 | Allen | ...................... | F22B 1/063 122/32 |
| 3,809,379 A * | 5/1974 | Carbonnel | ............. | B22D 35/00 266/208 |
| 4,164,253 A * | 8/1979 | Skala | .................... | F24H 7/0433 126/400 |
| 4,257,556 A * | 3/1981 | Skala | .................... | F24H 7/0433 165/10 |
| 4,519,447 A * | 5/1985 | Wiech, Jr. | ................ | H01L 23/13 165/104.23 |
| 4,824,329 A * | 4/1989 | Yamamoto | ........... | G21C 15/247 376/210 |
| 5,075,555 A * | 12/1991 | Woldseth | ................ | F25B 21/02 250/352 |
| 5,299,249 A * | 3/1994 | Burke | .................... | A61B 6/035 378/15 |
| 5,552,608 A * | 9/1996 | Gallagher | ............... | F17C 3/085 250/352 |
| 5,610,968 A * | 3/1997 | Deucher | ................ | A61B 6/035 378/199 |
| 5,913,358 A * | 6/1999 | Chadwick | .............. | B22D 18/04 164/119 |
| 6,491,428 B1 * | 12/2002 | Takanashi | ............... | A61B 6/035 378/199 |
| 7,126,741 B2 * | 10/2006 | Wagner | .................. | G02B 7/008 359/290 |
| 2003/0159811 A1 * | 8/2003 | Nurmi | ....................... | C01C 1/00 165/132 |
| 2004/0071259 A1 | 4/2004 | Lacey et al. | | |
| 2004/0264631 A1 | 12/2004 | Joshi et al. | | |
| 2005/0067579 A1 * | 3/2005 | Tsuchiya | ............... | G01T 1/2928 250/370.15 |
| 2005/0285046 A1 * | 12/2005 | Iwanczyk | ............... | H01L 31/02 250/370.15 |
| 2007/0221859 A1 * | 9/2007 | Nakata | .................... | A61B 6/502 250/370.15 |
| 2009/0084971 A1 * | 4/2009 | Ohta | .................... | A61B 6/0414 250/370.15 |
| 2011/0075786 A1 * | 3/2011 | McWhirter | ........... | F28D 1/0213 376/405 |
| 2011/0075787 A1 * | 3/2011 | McWhirter | ........... | F28D 1/0213 376/405 |
| 2011/0075788 A1 * | 3/2011 | McWhirter | ........... | F28D 7/0041 376/405 |
| 2011/0222642 A1 * | 9/2011 | Gautier | .................... | G21C 1/02 376/395 |
| 2011/0222649 A1 | 9/2011 | Hashimoto et al. | | |
| 2011/0311023 A1 | 12/2011 | Sagoh et al. | | |
| 2013/0037251 A1 * | 2/2013 | Joshi | ......................... | A61B 6/42 165/201 |
| 2013/0221228 A1 * | 8/2013 | Kuroda | ................. | G01T 1/2006 250/366 |
| 2014/0216693 A1 * | 8/2014 | Pekarsky | ........... | B60H 1/00278 165/104.31 |
| 2014/0295062 A1 * | 10/2014 | Chiyoma | ................ | G01T 1/202 427/74 |
| 2014/0314197 A1 * | 10/2014 | Watanabe | ............... | H01J 35/12 378/4 |
| 2016/0332505 A1 * | 11/2016 | Yamanaka | ............. | B60L 11/18 |

OTHER PUBLICATIONS

Machine Translation and First Office Action and Search issued in connection with corresponding CN Application No. 201410041478.9 dated Feb. 9, 2018.

Machine Translation and Notification of Reasons for Refusal issued in connection with corresponding JP Application No. 2016-547586 dated Aug. 7, 2018.

* cited by examiner

HEAT TRANSFER DEVICE, X-RAY DETECTING APPARATUS AND X-RAY IMAGING EQUIPMENT

CROSS REFERENCE TO RELATED APPLICATIONS

This application is a filing under 35 U.S.C. 371 of international application number PCT/US2015/011795, filed Jan. 16, 2015, which claims priority to Chinese application number 201410041478.9, filed on Jan. 28, 2014, the entire disclosures of each of which are hereby incorporated by reference in their entireties.

BACKGROUND OF THE INVENTION

The present invention relates to the field of X-ray imaging, to be more specific, relates to a heat transfer device, an X-ray detecting apparatus, and an X-ray imaging equipment. The X-ray imaging equipment usually comprises an X-ray generating apparatus and an X-ray detecting apparatus. The X-ray generating apparatus generates X-rays and irradiates the generated X-rays onto a target object to be imaged (e.g., a user to be diagnosed). The X-ray detecting apparatus receives the X-rays that pass through the target object and transforms the received X-rays into electrical signals. In addition, the X-ray imaging equipment can further comprise an image processing apparatus which processes the electrical signals transformed by the X-ray detecting apparatus to generate an image of the target object and a display apparatus for displaying the image generated by the image processing apparatus.

In order to ensure image quality of the X-ray imaging equipment, the X-ray detector in the X-ray detecting apparatus needs to operate at a constant temperature, e.g., 39° C.±1.5° C. Hence, the X-ray generating apparatus is equipped with a heat transfer device capable of adjusting temperature of the X-ray detector. The heat transfer device in the prior art usually comprises a resistance type heater for heating the X-ray detector and a radiator for cooling the X-ray detector and a fan for supplying air to the radiator. However, such heat transfer device is liable to be affected by the temperature condition of the ambient environment. For example, when the ambient temperature is relatively low, the current heat transfer device cannot effectively and/or rapidly heat the X-ray detector, and when the ambient temperature is relatively high, the current heat transfer device cannot effectively and/or rapidly cool the X-ray detector. Therefore, the X-ray detecting apparatus equipped with such heat transfer device is limited in terms of the operating environment, e.g., not higher than 34° C.

BRIEF SUMMARY OF THE INVENTION

The objective of the illustrative examples of the present invention is to overcome the above and/or other problems in the prior art. Hence, the illustrative examples of the present invention provide a heat transfer device, an X-ray detecting apparatus and an X-ray imaging equipment capable of improving heat transfer efficiency.

According to one illustrative example, a heat transfer device is provided. The heat transfer device comprises: a first heat transfer loop, configured to implement heat transfer with an X-ray detector; a heater, configured to heat a heat transfer fluid in the first heat transfer loop; a second heat transfer loop, disposed to implement heat transfer with the X-ray detector; a radiator, configured to cool the heat transfer fluid in the second heat transfer loop.

According to another illustrative example, an X-ray detecting apparatus is provided. The X-ray detecting apparatus comprises: an X-ray detector, configured to receive X-rays and to transform received X-rays into electrical signals; the heat transfer device as stated above, disposed on the relative surface of the X-ray detector opposite to the surface for receiving the X-rays.

According to a further illustrative example, an X-ray imaging equipment is provided. The X-ray imaging equipment comprises: an X-ray generating apparatus, configured to generate X-rays and to irradiate generated X-rays onto a target object to be imaged; the X-ray detecting apparatus as stated above, configured to receive X-rays that pass through the target object and to transform received X-rays into electrical signals for generating images of the target object.

Other features and aspects will become much clearer through the following detailed depictions, drawings and claims.

BRIEF DESCRIPTION OF THE DRAWINGS

The present invention can be better understood by depicting the illustrative examples of the present invention in combination with the following drawings.

DETAILED DESCRIPTION OF THE INVENTION

The specific embodiments of the present invention will be depicted below; it should be indicated that, during the process of specifically depicting these embodiments, in order to make a concise depiction, it is impossible for the present description to make detailed depiction to all features of the actual embodiments. It should be understood that, during the actual implementing process of any one embodiment, e.g., during the process of any one engineering project or designing project, in order to realize specific objectives of developers, and to meet system related or commerce related limits, usually various specific decisions will be made, such that a transition from one embodiment to another embodiment will also occur. In addition, it should also be understood that, although efforts as made during the developing process may be complicated and lengthy, for ordinary persons skilled in the art who are related with the contents disclosed by the present invention, some changes in design, manufacture or production on the basis of the technical contents disclosed by the present invention are only customary technical means, and should not be construed as the contents of the present invention being insufficiently disclosed.

Unless defined otherwise, the technical terms or scientific terms that are used in the claims and the description should have general meanings as understood by persons with ordinary skills in the technical field to which the present invention belongs. Such words as "first", "second" used in the description and claims of the present invention patent application do not denote any sequence, quantity or significance, and are only used to distinguish different constituting parts. Such words as "one" and "a (an)" only represent that at least one exists, without denoting quantity limitation. Such words as "including" or "comprising" mean that the elements or objects appearing before the words "including" or "comprising" cover the elements or objects and equivalent elements listed after the words "including" or "comprising", not excluding other elements or objects. Such words as "connection" or "link" are not limited to physical or mechanical connection, and are not limited to direct or indirect connections, neither.

Figure 1:
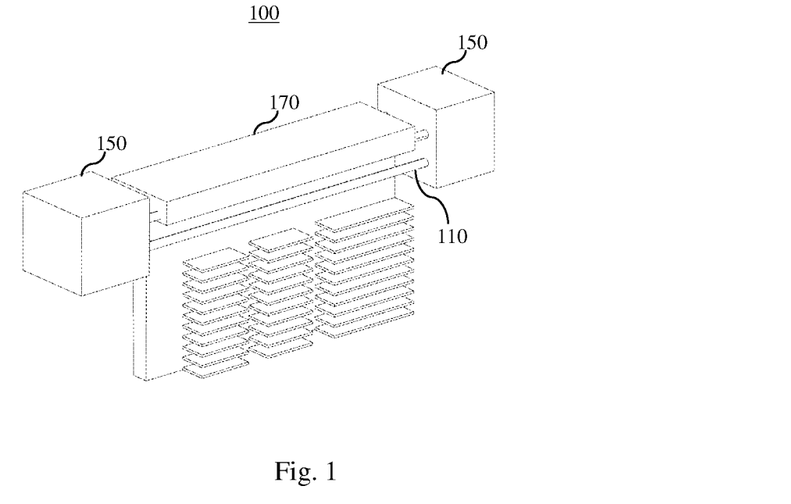
FIG. 1 provides a perspective view showing the heat transfer device according to an illustrative example.
Figure 2:
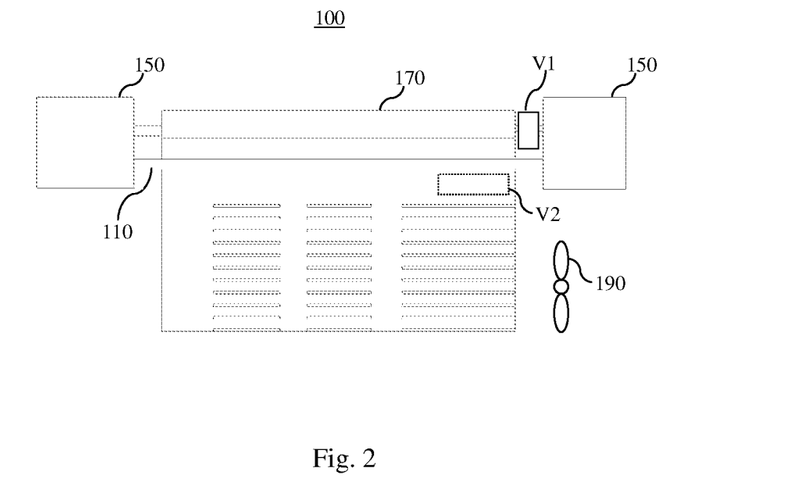
FIG. 2 provides a front view showing the heat transfer device according to an illustrative example.

FIG. 1 provides a perspective view showing the heat transfer device according to an illustrative example, and FIG. 2 provides a front view showing the heat transfer device according to an illustrative example. As shown in FIGS. 1 and 2, a heat transfer device 100 can comprise a first heat transfer loop 110, a second heat transfer loop 130 (see FIG. 4), a heater 150 and a radiator 170.

Figure 3:
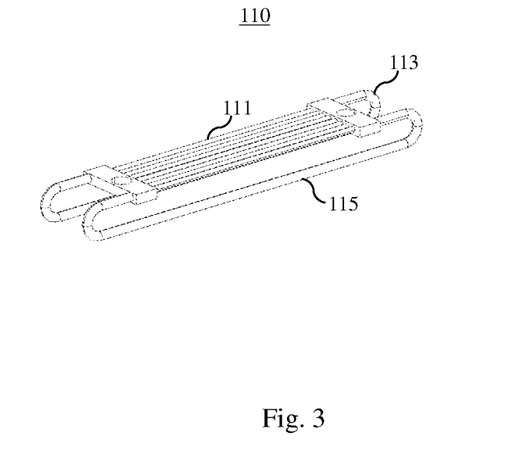
FIG. 3 provides a perspective view showing the first heat transfer loop according to an illustrative example.

FIG. 3 provides a perspective view showing the first heat transfer loop according to an illustrative example. As shown in FIG. 3, the first heat transfer loop 110 can comprise a first passage 111, a second passage 113 and a third passage 115 connecting the first passage 111 and the second passage 113. Hence, heat transfer fluid can flow through the first passage 111, the second passage 113 and the third passage 115, so as to circulate in the first heat transfer loop 110. Here, the heat transfer fluid can be water, organic solvent and liquid state metal alloy, etc. The liquid state metal alloy can have a lower viscosity coefficient and a higher thermal conductivity coefficient than water. For example, the liquid state metal alloy can be metal alloys in a liquid state at room temperature containing sodium, potassium and or other metals, such as NaK alloy.

Figure 9:
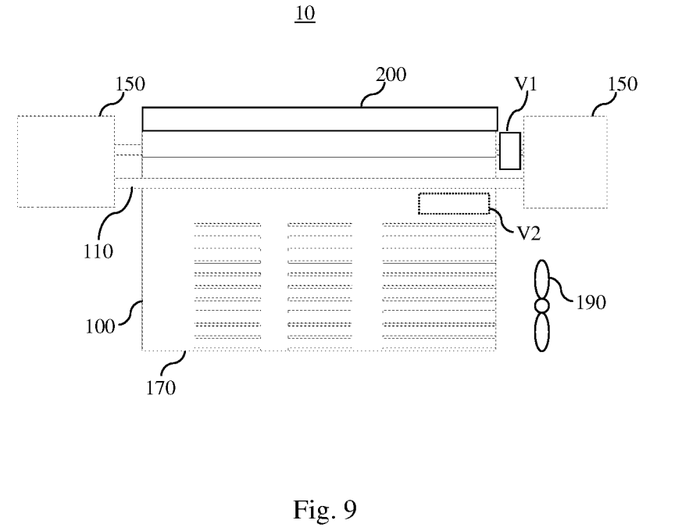
FIG. 9 provides a schematic diagram showing the X-ray detecting apparatus according to an illustrative example.

The first passage 111 can be disposed adjacent to the X-ray detector. As shown in FIG. 9, the second passage 113 can be disposed adjacent to the heater 150. Hence, the heat transfer fluid can implement heat transfer with the heater 150 when flowing through the second passage 113, so as to be heated by the heater 150. Then, the heat transfer fluid that has been heated by the heater 150 can flow through the third passage 115 to the first passage 111, so as to implement heat transfer with the X-ray detector, thereby heating the X-ray detector. As such, through circulation of the heat transfer fluid in the first heat transfer loop 110, the X-ray detector can be heated, so as to increase the temperature of the X-ray detector. In addition, in order to improve heat transfer efficiency between the heat transfer fluid and the X-ray detector, the first passage 111 can be set to comprise a plurality of sub-passages.

Figure 4:
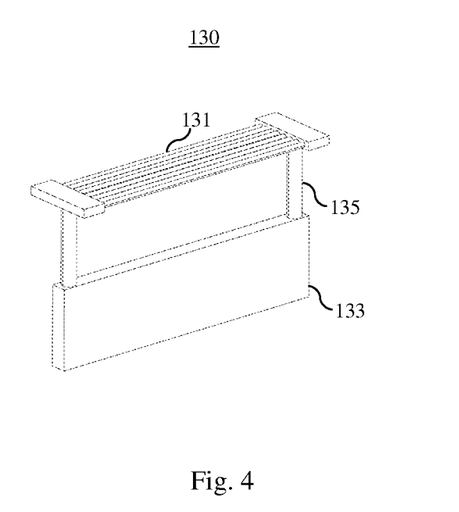
FIG. 4 provides a perspective view showing the second heat transfer loop according to an illustrative example.

FIG. 4 provides a perspective view showing the second heat transfer loop according to an illustrative example. As shown in FIG. 4, the second heat transfer loop 130 can comprise a fourth passage 131, a fifth passage 133 and a sixth passage 135 connecting the fourth passage 131 and the fifth passage 133. Hence, heat transfer fluid can flow through the fourth passage 131, the fifth passage 133 and the sixth passage 135, so as to circulate in the second heat transfer loop 130. The heat transfer fluid in the second heat transfer loop 130 can be different from or identical to the heat transfer fluid in the first heat transfer loop 110, e.g., the first heat transfer loop 110 and the second heat transfer loop 130 can comprise liquid state metal alloy.

The fourth passage 131 can be disposed adjacent to the X-ray detector; as shown in FIG. 9, the fifth passage 133 can be disposed adjacent to a second portion 173 of the radiator 170 comprising a plurality of radiator fins. Hence, the heat transfer fluid can implement heat transfer with the second portion 173 of the radiator 170 when flowing through the fifth passage 133, so as to be cooled by the second portion 173 of the radiator 170. Then, the heat transfer fluid that has been cooled by the second portion 173 can flow through the sixth passage 135 to the fourth passage 131, so as to implement heat transfer with the X-ray detector, thereby cooling the X-ray detector. As such, through circulation of the heat transfer fluid in the second heat transfer loop 130, the X-ray detector can be cooled, so as to reduce the temperature of the X-ray detector. In addition, in order to improve heat transfer efficiency between the heat transfer fluid and the X-ray detector, the fourth passage 131 can be set to comprise a plurality of sub-passages.

Figure 5:
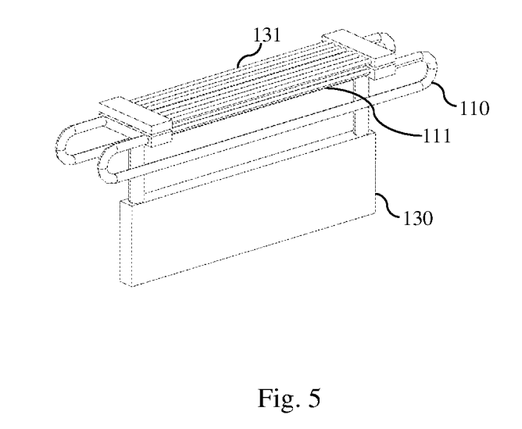
FIG. 5 provides a perspective view showing the state of assembling the first heat transfer loop and the second heat transfer loop together according to an illustrative example.

FIG. 5 provides a perspective view showing the state of assembling the first heat transfer loop and the second heat transfer loop together according to an illustrative example. As shown in FIG. 5, the fourth passage 131 of the second heat transfer loop 130 can be disposed between the X-ray detector and the first passage 111 of the first heat transfer loop 110. Hence, heat transfer efficiency between the first heat transfer loop 110 and the X-ray detector can be improved. However, the illustrative example is not exhaustive; in other illustrative examples, the first passage 111 of the first heat transfer loop 110 can be disposed between the X-ray detector and the fourth passage 131 of the second heat transfer loop 130.

Figure 6:
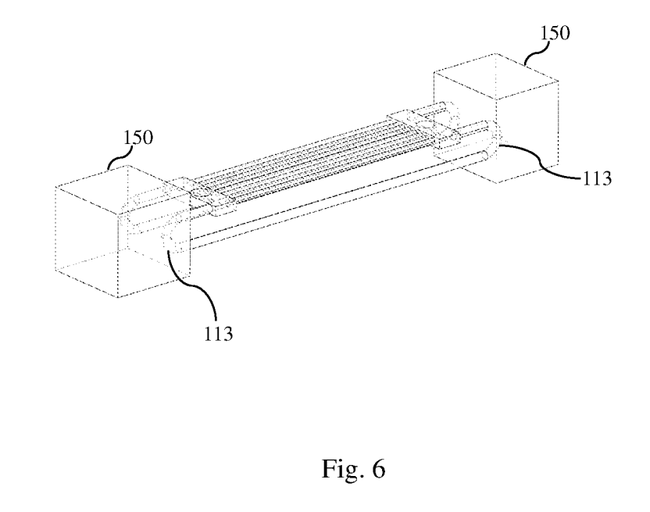
FIG. 6 provides a perspective view showing the state of assembling the first heat transfer loop and the heater together according to an illustrative example.

FIG. 6 provides a perspective view showing the state of assembling the first heat transfer loop and the heater together according to an illustrative example. As shown in FIG. 6, the heater 150 can be disposed at both sides of the first heat transfer loop 110 respectively. The heater 150 can comprise a heat transfer space filled with heating medium. Here, the heating medium can be pre-heated and injected into the heat transfer space of the heater 150. The heating medium can be such liquids as industrial oils or other organic solvents, etc. For example, the heating medium can be castor oil for industrial use. The second passage 113 of the first heat transfer loop 110 can enter the heat transfer space of the heater 150. Hence, the heat transfer fluid can implement heat transfer with the heating medium when flowing through the second passage 113.

Figure 7:
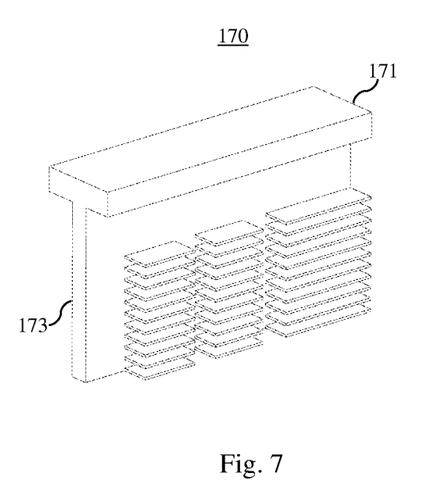
FIG. 7 provides a perspective view showing the radiator according to an illustrative example.
Figure 8:
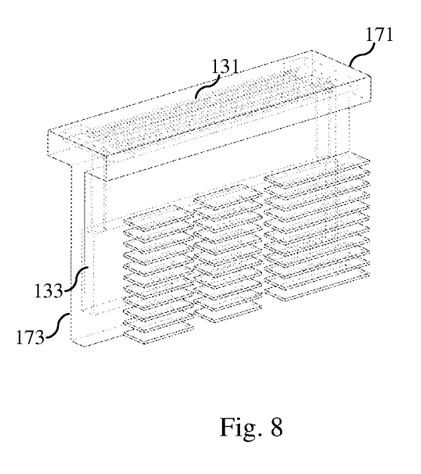
FIG. 8 provides a perspective view showing the state of assembling the second heat transfer loop and the radiator together according to an illustrative example.

FIG. 7 provides a perspective view showing the radiator according to an illustrative example, and FIG. 8 provides a perspective view showing the state of assembling the second heat transfer loop and the radiator together according to an illustrative example. As shown in FIGS. 7 and 8, the radiator 170 can comprise a first portion 171 in contact with the X-ray detector and a second portion 173 extending from the first portion and comprising a plurality of radiator fins. The fourth passage 131 of the second heat transfer loop 130 can be disposed in the first portion 171 of the radiator 170, so as to be adjacent to the X-ray detector. In addition, the fifth passage 133 of the second heat transfer loop 130 can be disposed in the second portion 173 of the radiator. Furthermore, the first passage 111 of the first heat transfer loop 110 can also be disposed in the first portion 171 of the radiator 170, so as to be adjacent to the X-ray detector.

The heat transfer device 100 can further comprise a fan 190, as shown in FIG. 2. The fan 190 can be disposed to be adjacent to the radiator 170 and to supply air to the radiator, thereby increasing radiation efficiency of the radiator 170. For example, the fan 190 can supply air to the second portion 173 having radiator fins, so as to further improve radiation efficiency of the radiator 170. In addition, as shown in FIG. 2, the heat transfer device 100 can further comprise electromagnetic pumps V1 and V2. The electromagnetic pumps V1 and V2 can control flow rate of heat transfer fluid in the first heat transfer loop 110 and the second heat transfer loop 130, respectively. Hence, when the X-ray detector needs to be heated, the electromagnetic pump V1 can operate, so as to enable the heat transfer fluid such as liquid state metal alloy to circulate in the first heat transfer loop 110 at a certain flow rate, thereby implementing heat transfer with the heater 150 and the X-ray detector; meanwhile, the electromagnetic pump V2 can operate, so as to prevent the heat transfer fluid in the second heat transfer loop 130 from circulating and flowing. On the contrary, when the X-ray detector needs to be cooled, the electromagnetic pump V2 can operate, so as to enable the heat transfer fluid to circulate in the second heat transfer loop 130 at a certain flow rate, thereby implementing heat transfer with the radiator 170 and the X-ray detector; meanwhile, the electromagnetic pump V1 can operate, so as to prevent the heat transfer fluid in the first heat transfer loop 110 from circulating and flowing. The electromagnetic pump V1 and the electromagnetic pump V2 can be disposed at an appropriate position respectively, so as to conduct the above controls to the flow rate of the fluid in the first heat transfer loop 110 and the second heat transfer loop 130. In an example, the electromagnetic pump V1 and the electromagnetic pump V2 can be disposed at the third passage 115 of the first heat transfer loop 110 and the sixth passage 135 of the second heat transfer loop 130, respectively. Here, it is well known that the flowing of the liquid state metal alloy can be controlled through magnetic fields produced by the electromagnetic pumps, so the corresponding contents are not described in details.

According to the illustrative example, the heat transfer device can comprise the first heat transfer loop and the second heat transfer loop, thereby increasing the heating efficiency of the heater to the X-ray detector and the cooling efficiency of the radiator to the X-ray detector. In addition, the first and second heat transfer loops can comprise liquid state metal alloy, thereby further increasing the heat transfer efficiency, and improving uniformity of temperature distribution of the X-ray detector. In addition, the following of liquid state metal alloy can be controlled by setting electromagnetic pumps, thereby simplifying the structure of the heat transfer device.

FIG. 9 provides a schematic diagram showing the X-ray detecting apparatus according to an illustrative example. Here, for the sake of conciseness, the depiction of elements same or similar to the elements as described above will be omitted.

As shown in FIG. 9, an X-ray detecting apparatus 10 can comprise the heat transfer device 100 as stated above and an X-ray detector 200. The X-ray detector 200 can receive X-rays and transform the received X-rays into electrical signals. The heat transfer device 100 can be disposed on the relative surface of the X-ray detector 200 opposite to the surface for receiving X-rays, so as to implement heat transfer with the X-ray detector 200, thereby keeping the temperature of the X-ray detector 200 constant.

Figure 10:
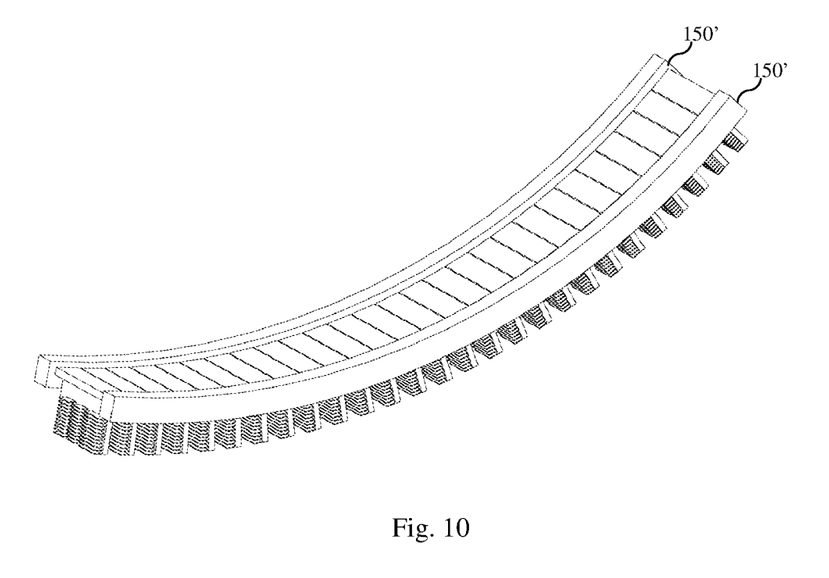
FIG. 10 provides a perspective view showing the plurality of heat transfer devices comprising heaters in connection with each other included in the X-ray detecting apparatus according to an illustrative example.

The X-ray detecting apparatus 10 can comprise a plurality of X-ray detectors 200, e.g., the number of X-ray detectors can be 64, 128, 256, etc. Although FIG. 10 shows that one X-ray detector 200 corresponds to one heat transfer device 100, the illustrative example is not exhaustive, and one heat transfer device 100 can correspond to two or more above X-ray detectors 200. That is, one heat transfer device 100 can be disposed on the relative surfaces of two or more X-ray detectors 200.

FIG. 10 provides a perspective view showing the plurality of heat transfer devices comprising heaters in connection with each other included in the X-ray detecting apparatus according to an illustrative example. In an illustrative example, when the X-ray detecting apparatus 10 comprises a plurality of heat transfer devices 100, heat transfer spaces of the heaters 150 of the plurality of heat transfer devices 10 located at the same side can be in connection with each other; in FIG. 10, the reference sign 150' represents heaters connected as such. Hence, heating medium can flow among heaters 150 in connection with each other. Thus, the structure of the X-ray detecting apparatus 10 can be simplified, and the heat transfer devices 100 having heat transfer spaces connected with each other can uniformly provide heat to the corresponding X-ray detectors.

Figure 11:
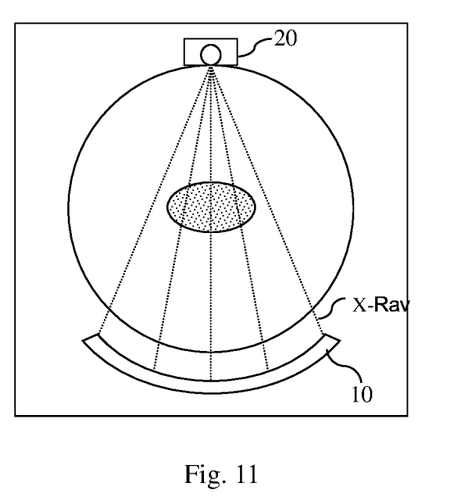
FIG. 11 provides a schematic diagram showing the X-ray imaging equipment according to an illustrative example.

FIG. 11 provides a schematic diagram showing the X-ray imaging equipment according to an illustrative example. Here, for the sake of conciseness, the depiction of elements same or similar to the elements as described above will be omitted.

As shown in FIG. 11, an X-ray imaging equipment can comprise the X-ray detecting apparatus 10 as stated above and an X-ray generating apparatus 20. The X-ray generating apparatus 20 can generate X-rays, and can irradiate the generated X-rays onto a target object to be imaged (e.g., a user to be diagnosed). The X-ray detecting apparatus 10 can receive X-rays that pass through the target object, and can transform the received X-rays into electrical signals for generating images of the target object. In addition, though not shown in FIG. 11, the X-ray imaging equipment can further comprise an image processor which processes the electrical signals transformed by the X-ray detecting apparatus 10 to generate an image of the target object, and a display for displaying the image generated by the image processor.

According to an illustrative example, the heat transfer device can implement heat transfer with the X-ray detector in the X-ray detecting apparatus with an improved heat transfer efficiency, so as to keep the temperature of the X-ray detector constant. Therefore, the X-ray detecting apparatus and the X-ray imaging equipment equipped with such heat transfer device can be operated under the conditions having a relatively wide ambient temperature range.

Some illustrative examples have been depicted above. However, it can be understood that various amendments can be made. For example, if the technology as depicted is executed in a different order, and/or, if the assemblies in the system, framework, device or electric circuit as depicted are combined in a different manner and/or substituted or supplemented by additional assemblies or their equivalents, an appropriate result can be achieved. Accordingly, other embodiments all fall within the protection scopes of the claim.

We claim:

1. A heat transfer device, comprising:
a first heat transfer loop, configured to implement heat transfer with an X-ray detector;
at least one heater coupled to the first heat transfer loop, configured to heat a heat transfer fluid in the first heat transfer loop;
a first electromagnetic pump, configured to control flow rate of the heat transfer fluid in the first heat transfer loop;
a second heat transfer loop separate from but adjacent to and integrated with the first heat transfer loop, configured to implement heat transfer with the X-ray detector;
a radiator coupled to the second heat transfer loop, configured to cool the heat transfer fluid in the second heat transfer loop;
a second electromagnetic pump, configured to control flow rate of the heat transfer fluid in the second heat transfer loop;
wherein the first heat transfer loop comprises:
a first passage adjacent to the X-ray detector;
a second passage adjacent to the heater; and
a third passage connecting the first passage and the second passage;
wherein the heat transfer fluid in the first heat transfer loop implements heat transfer with the X-ray detector when flowing through the first passage, and implements heat transfer with the heater when flowing through the second passage;
wherein the second heat transfer loop comprises:
a fourth passage adjacent to the X-ray detector;
a fifth passage adjacent to the radiator; and
a sixth passage connecting the fourth passage and the fifth passage;
wherein the heat transfer fluid in the second heat transfer loop implements heat transfer with the X-ray detector when flowing through the fourth passage, and implements heat transfer with the radiator when flowing through the fifth passage;
wherein the first passage of the first heat transfer loop and the fourth passage of the second heat transfer loop comprise a plurality of sub-passages, respectively; and
wherein the fourth passage of the second heat transfer loop is disposed between the X-ray detector and the first passage of the first heat transfer loop.

2. The heat transfer device according to claim 1, wherein a first heater is disposed on a first side of the first heat transfer loop and a second heater is disposed on a second side of the first heater transfer loop, the second side is opposite the first side, and the first and second heaters comprise heat transfer spaces filled with heat transfer fluid, and the second passage of the first heat transfer loop is disposed in the heat transfer spaces of the first and second heaters, such that the heat transfer fluid implements heat transfer with the first and second heaters when flowing through the second passage.

3. The heat transfer device according to claim 1, wherein the radiator comprises a first portion in contact with the X-ray detector and a second portion extending from the first portion and comprising a plurality of radiator fins, the first passage of the first heat transfer loop and the fourth passage of the second heat transfer loop are disposed in the first portion of the radiator, and the fifth passage of the second heat transfer loop is disposed in the second portion of the radiator.

4. The heat transfer device according to claim 1, wherein the heat transfer device further comprises:
a fan, disposed adjacent to the radiator and supplying air to the radiator.

5. The heat transfer device according to claim 1, wherein the heat transfer fluid is a liquid state metal alloy.

6. An X-ray detecting apparatus, comprising:
an X-ray detector, configured to receive X-rays and to transform received X-rays into electrical signals;
a heat transfer device comprising a first heat transfer loop, configured to implement heat transfer with the X-ray detector; a heater coupled to the first heat transfer loop, configured to heat a heat transfer fluid in the first heat transfer loop; a second heat transfer loop separate from but adjacent to and integrated with the first heat transfer loop, configured to implement heat transfer with the X-ray detector; and a radiator coupled to the second heat transfer loop, configured to cool the heat transfer fluid in the second heat transfer loop;
wherein the heat transfer device is disposed on a first surface of the X-ray detector, the first surface being opposite to a surface of the X-ray detector that receives X-rays;
wherein the first heat transfer loop comprises:
a first passage adjacent to the X-ray detector;
a second passage adjacent to the heater; and
a third passage connecting the first passage and the second passage;
wherein the heat transfer fluid in the first heat transfer loop implements heat transfer with the X-ray detector when flowing through the first passage, and implements heat transfer with the heater when flowing through the second passage;
wherein the second heat transfer loop comprises:
a fourth passage adjacent to the X-ray detector;
a fifth passage adjacent to the radiator; and
a sixth passage connecting the fourth passage and the fifth passage;
wherein the heat transfer fluid in the second heat transfer loop implements heat transfer with the X-ray detector when flowing through the fourth passage, and implements heat transfer with the radiator when flowing through the fifth passage;
wherein the first passage of the first heat transfer loop and the fourth passage of the second heat transfer loop comprise a plurality of sub-passages, respectively; and
wherein the fourth passage of the second heat transfer loop is disposed between the X-ray detector and the first passage of the first heat transfer loop.

7. The X-ray detecting apparatus according to claim 6, wherein the X-ray detecting apparatus comprises a plurality of X-ray detectors and a plurality of heat transfer devices respectively disposed on the first surface of at least one of the plurality of X-ray detectors.

* * * * *